United States Patent
Choi et al.

(10) Patent No.: US 10,043,641 B2
(45) Date of Patent: Aug. 7, 2018

(54) METHODS AND APPARATUS FOR PROCESSING CHAMBER CLEANING END POINT DETECTION

(71) Applicant: Applied Materials, Inc., Santa Clara, CA (US)

(72) Inventors: Young-Jin Choi, San Jose, CA (US); Su Ho Cho, Santa Clara, CA (US); Beomsoo Park, San Jose, CA (US); Fei Peng, San Jose, CA (US); Soo Young Choi, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 15/273,631

(22) Filed: Sep. 22, 2016

(65) Prior Publication Data

US 2018/0082827 A1     Mar. 22, 2018

(51) Int. Cl.
| | |
|---|---|
| *H01J 37/32* | (2006.01) |
| *G01N 21/73* | (2006.01) |
| *C23C 16/50* | (2006.01) |
| *C23C 16/455* | (2006.01) |

(52) U.S. Cl.
CPC ...... *H01J 37/32963* (2013.01); *C23C 16/455* (2013.01); *C23C 16/50* (2013.01); *G01N 21/73* (2013.01); *H01J 37/32853* (2013.01); *H01J 37/32926* (2013.01); *G01N 2201/06113* (2013.01); *H01J 2237/335* (2013.01)

(58) Field of Classification Search
CPC .......... H01J 37/32963; H01J 2237/335; C23C 16/455; C23C 16/50; G01N 21/73; G01N 2201/06113
See application file for complete search history.

(56) References Cited

U.S. PATENT DOCUMENTS

| | | |
|---|---|---|
| 5,712,702 A | 1/1998 | McGahay et al. |
| 6,052,176 A | 4/2000 | Ni et al. |
| 6,124,927 A | 9/2000 | Zhong et al. |
| 6,170,492 B1 | 1/2001 | Ueda et al. |

(Continued)

FOREIGN PATENT DOCUMENTS

| | | |
|---|---|---|
| WO | WO 99/64814 | 12/1999 |
| WO | WO2016171845 | 10/2016 |

OTHER PUBLICATIONS

International Search Report and Written Opinion of International Application No. PCT/US2017/051630 dated Dec. 21, 2017.

*Primary Examiner* — Dominic J Bologna

(74) *Attorney, Agent, or Firm* — Dugan & Dugan, PC

(57) ABSTRACT

Embodiments provide systems, methods and apparatus for detecting a cleaning endpoint of a cleaning process performed within a processing chamber. Embodiments include a spectrometer adapted to measure a spectrum response over time of a cleaning reaction within a processing chamber during a cleaning process; and a lens system coupled to the spectrometer and disposed to focus on a selected area within the processing chamber via a viewport and to amplify intensity of radiation from the selected area during the cleaning process. The selected area is chosen based on being the expected location of the last cleaning reaction during the cleaning process within the processing chamber (e.g., a corner in a rectangular chamber). Numerous other aspects are provided.

20 Claims, 6 Drawing Sheets

(56) References Cited

U.S. PATENT DOCUMENTS

| | | | |
|---|---|---|---|
| 6,297,064 B1* | 10/2001 | Koshimizu | G01N 21/68 216/60 |
| 6,881,276 B2 | 4/2005 | Blonigan et al. | |
| 2005/0241669 A1 | 11/2005 | Wodecki | |
| 2011/0070741 A1 | 3/2011 | Nakayama | |
| 2012/0103936 A1* | 5/2012 | Grimbergen | H01J 37/32963 216/41 |
| 2012/0273005 A1 | 11/2012 | Ramachandran et al. | |
| 2015/0221503 A1* | 8/2015 | Toyoda | H01J 37/3244 438/758 |
| 2015/0221507 A1* | 8/2015 | Won | H01L 21/02565 438/104 |
| 2016/0314944 A1 | 10/2016 | Bhatia et al. | |

\* cited by examiner

METHODS AND APPARATUS FOR PROCESSING CHAMBER CLEANING END POINT DETECTION

FIELD

Embodiments of the present invention relate to electronic device processing chambers, and more specifically to methods and apparatus for chamber cleaning end point detection.

BACKGROUND

Chemical vapor deposition (CVD) is widely used in the semiconductor industry to deposit films of various kinds, such as intrinsic and doped amorphous silicon (a-Si), silicon oxide ($Si_xO_y$), silicon nitride ($Si_xN_s$), silicon oxynitride, and the like on a substrate. Semiconductor CVD processing is generally done in a vacuum chamber by using precursor gases which dissociate and react to form the desired film. In order to deposit films at low temperatures and relatively high deposition rates, a plasma may be formed from the precursor gases in the chamber during the deposition. One type of such plasma processes is plasma enhanced CVD (PECVD). Another type of such plasma processes is high density plasma CVD (HDP-CVD).

Many processing chambers are made of aluminum and include a support for the substrate and a port for entry of the required precursor gases. When a plasma is used, the gas inlet and/or the substrate support is connected to a source of power, such as a radio frequency (RF) power source. A vacuum pump is also connected to the chamber to control the pressure in the chamber and to remove the various gases and contaminants generated during the deposition.

In electronic device processing, it is desirable to keep contaminants in the chamber to a minimum. During the deposition process however, the film is deposited not only on the substrate, but also on walls and various components, e.g., shields, the substrate support and the like, within the chamber. During subsequent depositions, the film on the walls and various components can crack or peel, causing contaminants to fall on the substrate. This causes problems and damage to particular devices on the substrate. Damaged devices have to be discarded.

When large glass substrates are processed, for example, to form thin film transistors for use in flat panel displays and the like, more than a million transistors may be formed on a single substrate. The presence of contaminants in the processing chamber can be even more problematic in this case, since the flat panel display is likely to be inoperative if damaged by particulates. In this case, an entire large glass substrate may have to be discarded.

Thus, processing chambers are periodically cleaned to remove accumulated films from prior depositions. Cleaning may be performed by passing an etch gas, for example a fluorine-containing gas, such as nitrogen trifluoride ($NF_3$), into the chamber. A standard method of performing this cleaning procedure is to pass a constant flow of $NF_3$ into the chamber. A plasma is initiated from the fluorine-containing gas which reacts with coatings from prior depositions on the chamber walls and fixtures, e.g., coatings of Si, $Si_xO_y$, $Si_xON$ and the like, as well as any other materials in the chamber. In particular, the $NF_3$ creates free fluorine radicals "F*" which react with Si-containing residues.

Alternatively, many electronic device processing chambers, use a remote plasma cleaning system (RPCS) for removing residual accumulation from the inside of the chamber after substrate processing. During cleaning, a remote plasma source (RPS) is coupled to the processing chamber and plasma (e.g., a fluorine-containing gas plasma such as NF3) is fed into the chamber to react with the residues from prior depositions. The resulting gases are then pumped out of the chamber via an exhaust outlet.

The frequency and duration of a cleaning cycle were typically determined by trial and error or using historical data. For instance, a chamber may be scheduled for cleaning after processing a predetermined number of substrates, regardless of the condition of the chamber. With respect to duration, it can be difficult to accurately determine when the cleaning has completed. To insure that the chambers are thoroughly cleaned, an extra 20 to 30 percent of the expected cleaning time may be added to the cleaning cycle, without regard to considering the damage that the extra cleaning time may cause to the chamber and the components contained therein. Thus, what is needed are improved methods and apparatus for detecting the cleaning end point.

SUMMARY

In some embodiments, a method for processing chamber cleaning end point detection is provided. The method includes performing a cleaning process within a processing chamber; focusing a lens system on a selected area within the processing chamber via a viewport during the cleaning process; amplifying an intensity of radiation from a cleaning reaction at the selected area during the cleaning process; and measuring a spectrum response over time of a cleaning reaction within the processing chamber during the cleaning process using a spectrometer coupled to the lens system. The selected area is chosen based on being an expected location of a last cleaning reaction during the cleaning process within the processing chamber.

In other embodiments, a system for processing substrates is provided. The system includes a processing chamber operative to process substrates; and a cleaning endpoint detection apparatus including a spectrometer adapted to measure a spectrum response over time of a cleaning reaction within the processing chamber during a cleaning process and a lens system coupled to the spectrometer and disposed to focus on a selected area within the processing chamber via a viewport and to amplify intensity of radiation from a cleaning reaction at the selected area during the cleaning process. The selected area is chosen based on being an expected location of a last cleaning reaction during the cleaning process within the processing chamber.

In still other embodiments, an apparatus for processing chamber cleaning end point detection is provided. The apparatus includes a spectrometer adapted to measure a spectrum response over time of a cleaning reaction within a processing chamber during a cleaning process; and a lens system coupled to the spectrometer and disposed to focus on a selected area within the processing chamber via a viewport and to amplify intensity of radiation from the selected area during the cleaning process. The selected area is chosen based on being an expected location of a last cleaning reaction during the cleaning process within the processing chamber.

In some other embodiments, a computer readable medium may be provided having instructions stored thereon that, when executed, cause a processing system to perform a method of monitoring a cleaning process being performed in a processing chamber to detect a cleaning endpoint. The method may include any of the embodiments disclosed herein.

Numerous other aspects are provided in accordance with these and other aspects of the invention. Other features and aspects of the present invention will become more fully apparent from the following detailed description, the appended claims and the accompanying drawings. To facilitate understanding, identical reference numerals have been used, where possible, to designate identical elements that are common to the drawings. The drawings are not drawn to scale and may be simplified for clarity. It is contemplated that elements and features of one embodiment may be beneficially incorporated in other embodiments without further recitation.

DESCRIPTION

Figure 1:
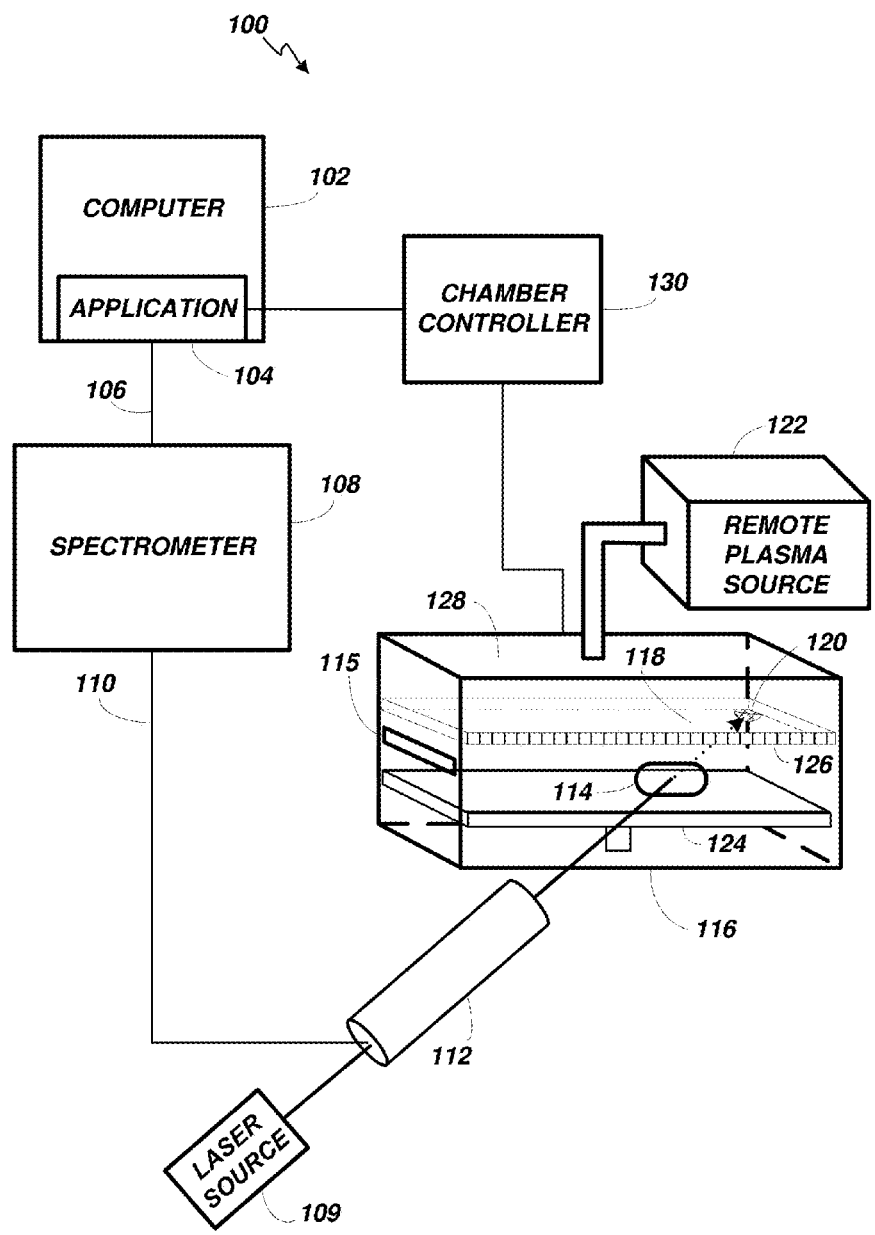
FIG. 1 is a diagram depicting an example of a processing chamber cleaning end point detection system according to embodiments of the present invention.

Embodiments of the present invention relate to methods and apparatus for determining an endpoint of a processing chamber cleaning process. Embodiments of the methods and apparatus may advantageously provide accurate endpoint detection for a cleaning process such that wear on processing chamber components from the cleaning process may be minimized while minimizing process drift and defects due to insufficient processing chamber cleaning. For the purposes of promoting an understanding of the principles of embodiments of the invention, reference will now be made to the examples illustrated in the drawings and specific language will be used to describe the same. It will nevertheless be understood that no limitation of the scope of the invention is thereby intended, and any alterations and further modifications in the illustrated embodiments, and any further applications of the principles of the invention as illustrated therein as would normally occur to one skilled in the art to which the invention relates are contemplated herein.

Embodiments of the present invention provide systems, apparatus and methods for accurately determining when an electronic device processing chamber has been thoroughly cleaned. In other words, embodiments provide systems, apparatus and methods for detecting an optimal cleaning endpoint. Instead of performing a cleaning cycle for an extended time to insure that a chamber is thoroughly cleaned at the expense of excess wear on the chamber which results in degradation of "system tunable availability and consistency tradeoffs" (TACT) which increases the cost of operation (COO), the excess expense of the gases and energy used, and the excess expense of the extra time itself, embodiments of the present invention use a spectrometer with an amplified optical signal (e.g., using magnifying lenses) to monitor an area within the processing chamber that will be the last to be completely cleaned. For example, depending on the geometry of the chamber and where the cleaning plasma (or other cleaning chemistry) is supplied/directed within the chamber, a corner or edge area of the chamber may take the most time to clean using plasma (or other cleaning reaction). Thus, embodiments of the present invention focus detection of cleaning reactants at a point where the last cleaning reactions are expected.

Unlike prior art systems that attempt to detect cleaning reactants in the flow moving through the exhaust outlet, embodiments of the present invention provide a substantially more sensitive method of determining whether the chamber is clean. Monitoring the exhaust outlet for reactants, particularly when the chambers have sufficient volume to accommodate large substrates, is difficult because particularly with larger chambers, the concentration of reactant particles drops off to the point that they become difficult to reliably detect while the last (e.g., corner) areas are being cleaned. Thus, prior art methods of monitoring exhaust may not provide a clear indication of when the chamber is clean and it may be necessary to extend the cleaning time to insure thorough cleaning. In contrast, embodiments of the present invention reduce material costs and improve TACT by providing a precise indication when the cleaning endpoint has been reached.

Embodiments of the present invention are depicted in the example system 100 illustrated in FIG. 1. In some embodiments, a computer 102 (e.g., a personal computer, main frame, controller, processor, etc.) executing an application 104 is communicatively coupled (e.g., via a wired connection 106 such as a universal serial bus (USB) cable or via a wireless connection such as WLAN) to a spectrometer 108. In some embodiments, the spectrometer 108 can include a computer 102 integrated within the housing of the spectrometer 108.

The spectrometer 108 can also include a light source, such as a laser, for projecting onto a target cleaning reaction site whose spectral response is to be measured. In some embodiments, a laser with a wavelength of approximately 635 nm (i.e., red), approximately 520 nm (i.e., green) or approximately 445 nm (i.e., blue) can be used. In some embodiments as shown in FIG. 1, any commercially available laser source 109 separate from the spectrometer 108 can be used including for example, a common laser pointer. Note that the laser is used to help initially target the area to be monitored during the cleaning process but is turned off during the actual monitoring of the cleaning process. Other methods of targeting can be used in place of a laser and thus, the laser source 109 is optional. For example, a mechanical frame can be used for targeting.

The spectrometer 108 is coupled via a fiber optic cable (e.g., optical fiber 110) to a magnifying zoom lens 112. The laser source 109 can also be coupled to the zoom lens 112 via a fiber optic cable or, as shown, can simply be aimed through the zoom lens 112.

The zoom lens 112 can be embodied as a multi-lens system that can magnify the target by approximately two times to approximately twenty times and amplify the intensity of the spectrum response approximately three times to approximately ten times. Other magnifications and amplifications can be used. An example of a commercially available zoom lens suitable for use with embodiments of the present invention include the model VZM™ 1000i Zoom Imaging Lens manufactured by Edmund Optics of Barrington, N.J., USA. Other commercially available lens systems can also be fitted with an adapter to be used with embodiments of the present invention.

The zoom lens 112 is aimed through a view port 114 of the processing chamber 116 so that the laser beam 118 emitted by the spectrometer 108 (or other laser source 109) projects a beam spot 120 on a selected target area within the processing chamber 116. Note that the beam spot 120 is used for focusing (e.g., adjusting magnification, field of view, etc.) the zoom lens 112 on the selected target area and verifying the spectrometer 108 and zoom lens 112 are properly aligned. The laser beam 118 is turned off during monitoring of the cleaning. The view port 114 may be disposed so as to provide a direct, unobstructed line of sight to the selected target area from outside of the processing chamber 116. Although the zoom lens 112 is shown spaced from the view port 114 for clarity in FIG. 1, the zoom lens 112 can be disposed immediately adjacent, or in contact with, the view port 114. In some embodiments, the view port 114 is positioned on a side of the processing chamber 116 at a level between the chamber's electrodes (e.g., the diffuser plate and the susceptor) or the main plasma processing region of the processing chamber 116. In some embodiments, the zoom lens 112 may be disposed at an angled orientation relative to the plane of the view port 114 to allow the zoom lens 112 to be aimed at the selected area. In some embodiments, a shroud, adapter, or coupling (not shown) may be used between the zoom lens 112 and the view port 114 to both limit ambient light from reaching the spectrometer 108 and to more easily facilitate precise alignment and aiming of the zoom lens 112. In some embodiments, an adapter and/or frame can be used to securely mount the zoom lens 112 to the processing chamber 116 and to hold it in position.

The zoom lens 112 can be configured to have a focus area on the location of the beam spot 120 of approximately 100 nm by approximately 100 nm to approximately 200 nm by approximately 200 nm. In some embodiments, the focus area can be approximately 150 nm by approximately 150 nm. Other focus area sizes can be used. By using a smaller focus area, the system is made more sensitive and can have increased end point detection performance. However, a smaller focus area is more vulnerable to position shifting which can induce misdetection and reduced end point accuracy. Using a wider focus area allows coverage of a larger area for detection of the end point, but signal intensity may be weaker than when using a smaller focus area. The use of the laser beam 118 during initial set up allows very accurate targeting and focusing of the spectrometer 108/zoom lens 112 on a relatively small focus area (e.g., approximately 150 nm by approximately 150 nm). Use of the laser beam 118 also allows verification that the zoom lens 112 is properly aligned and focused between cleaning cycles.

In some embodiments, more than one spectrometer 108 and/or zoom lens 112 can be used to target different selected areas within the processing chamber. For example, if it is not certain where the last cleaning reaction will be, a first spectrometer 108/zoom lens 112 pair can be targeted at a first expected last reaction location and other pairs can be targeted at other expected last reaction locations.

A remote plasma source (RPS 122) may be coupled to the processing chamber 116 to supply cleaning plasma to the processing chamber 116 during cleaning. The processing chamber 116 also includes a susceptor 124 for supporting a substrate (not shown) and a diffuser plate 126 for distributing deposition gas during processing. The susceptor 124 and the diffuser plate 126 are coupled to a radio frequency (RF) energy supply (not shown) and also function as electrodes to excite the processing gases to plasma during processing. A processing gas supply (not shown) is also coupled to the processing chamber 116 via a backing plate 128.

In some embodiments as shown in FIG. 1, the cleaning plasma may also be supplied through the backing plate 128 toward the diffuser plate 126. Thus, in this arrangement, the cleaning reaction of a dissociated gas ($NF_3$, $CF_4$, or other gas) in the plasma with residue film, spreads from the center of the chamber out toward the chamber edges and finally into the corners of the chamber. Therefore, in a rectangular chamber (e.g., for processing glass substrates for flat panel displays), the corners of the diffuser plate 126 and the susceptor 124 (and shadow frame) are the last areas to be cleaned. In a circular type chamber, cleaning gas supplied from a center location typically results in a reaction that flows outward toward the walls of the chamber symmetrically. Thus, the chamber wall area (i.e., outer edge) is the area where the last cleaning reaction occurs just before the cleaning end point is reached. Therefore, the wall area can be selected/used as the target for monitoring with the zoom lens 112/spectrometer 108.

In alternative embodiments, the cleaning plasma may be supplied laterally (e.g., from the side) into the processing region between the susceptor 124 and the diffuser plate 126. In this arrangement, the cleaning reaction may traverse from one side of the chamber to the other (and then out to the far corners if the chamber is rectangular). In yet other alternative embodiments, the cleaning plasma may be supplied laterally (e.g., from the side) between the diffuser plate 126 and the backing plate 128. As with the prior embodiment, the cleaning reaction may traverse from one side of the chamber to the other (and then out to the far corners if the chamber is rectangular).

Operation of the processing chamber 116 is controlled via a chamber controller 130 which is communicatively coupled to the control inputs and sensors of the processing chamber 116 as well as to the RPS 122. For example, the chamber controller 130 can control operation of the slit valve 115 for loading a substrate into the processing chamber 116. In some embodiments, the cleaning process can use plasma exclusively from the RPS 122 and in other embodiments, the processing chamber 116 can generate a cleaning plasma along with the RPS 122 (e.g., called "plasma assist") or without the RPS 122. The chamber controller 130 can be communicatively coupled to the computer 102 to indicate to the application 104 that cleaning has commenced and to receive a signal from the application 104 that the cleaning endpoint has been detected. In some embodiments, the chamber controller 130 can be implemented within or as part of the computer 102.

In alternate embodiments, the processing chamber 116 may be adapted for performing at least one of deposition processes, etch processes, plasma enhanced deposition and/or etch processes, and thermal processes, among other processes performed in the manufacture of integrated semiconductor devices and circuits. Specifically, such processes may include, but are not limited to, rapid thermal processes (RTPs), chemical vapor deposition (CVD) processes, annealing processes, and the like.

Figure 2:
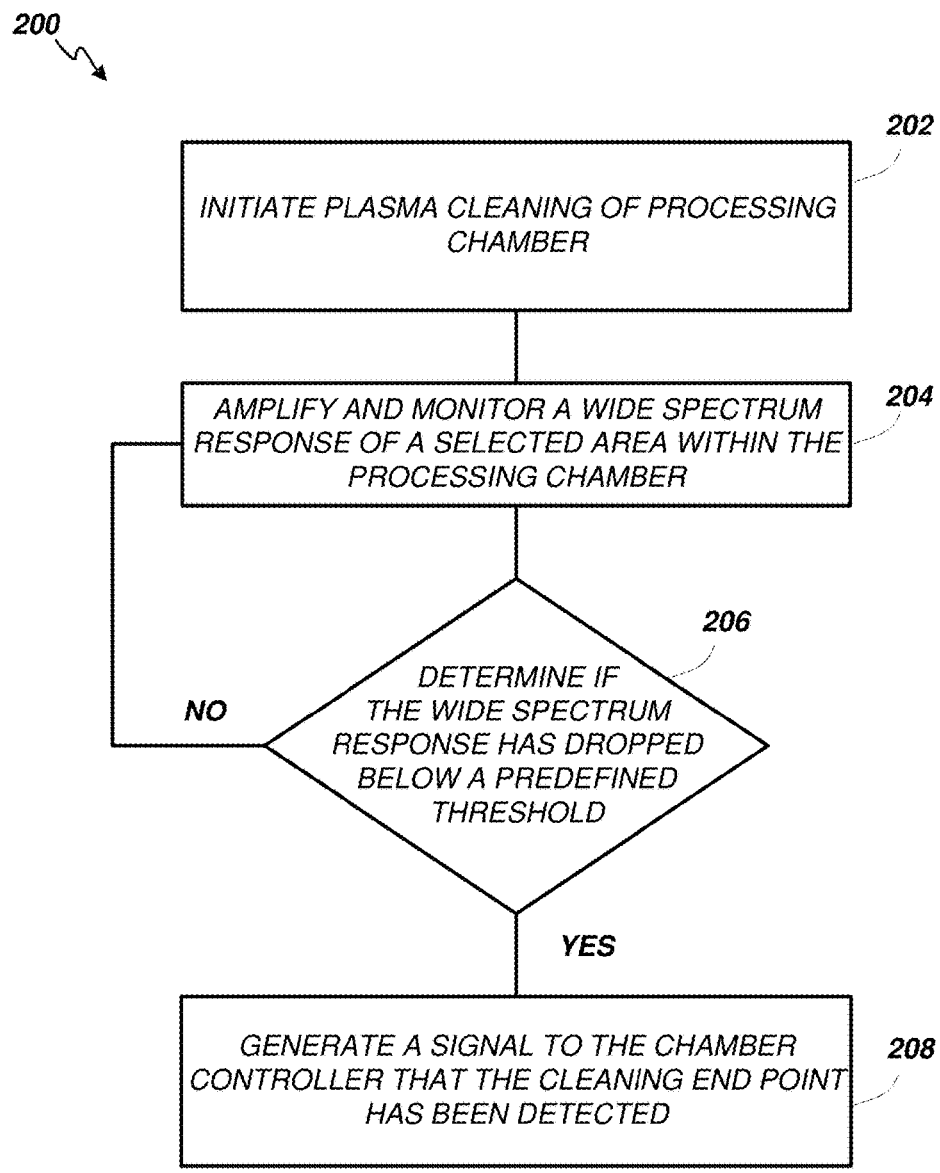
FIG. 2 is flowchart depicting an example of a processing chamber cleaning end point detection method according to embodiments of the present invention.

A method 200 of detecting a processing chamber cleaning endpoint is illustrated in the flowchart of FIG. 2. In operation, cleaning of the processing chamber 116 is initiated by flowing plasma from the RPS 122 into the processing chamber 116 (202). An optically magnified spectrometer 108 is used to amplify and monitor a wide spectrum response of a selected area within the processing chamber 116 that is expected to be the last area to be cleaned by the cleaning plasma (e.g., the expected site of the last cleaning reaction) (204).

In some embodiments with a rectangular processing chamber 116 for example, the monitored area is a corner of the diffuser plate 126 or a corner of the susceptor 124. In some embodiments, the monitored area is a corner of a shadow frame on the susceptor 124. In some embodiments with a circular processing chamber 116, the monitored area is a wall of the processing chamber 116. If the cleaning reaction tends to end last at the upper edge of the wall (e.g., where the wall meets the lid of the processing chamber), the upper edge of the wall is the area selected for monitoring. Likewise, if the cleaning reaction tends to end last at the lower edge of the wall (e.g., where the wall meets the floor of the processing chamber), the lower edge of the wall is the area selected for monitoring.

A laser beam from the spectrometer 108 (or other source 109) is projected into the processing chamber 116 through the zoom lens 112 to help target the zoom lens 112 onto the selected area during initial set up. The zoom lens 112 is focused on the selected area of the beam spot 120 during initial set up and adapted to gather radiation from a cleaning reaction at the selected location (where the beam spot 120 was) during cleaning. The zoom lens 112 also directs the gathered radiation back to the spectrometer 108 via the optical fiber 110.

An application 104 executing on the computer 102 receives a signal from the spectrometer 108 representing the amplified wide spectrum (e.g., ultraviolet, visible, infrared, etc.) response over time of the cleaning reaction at the selected area and waits for the spectrum response to drop below a threshold indicating the absence of cleaning plasma reactants and the detection of the cleaning endpoint (206). In some embodiments, the threshold can be a predefined value determined by measuring the wide spectrum response of a clean processing chamber 116. In some embodiments, based on the cleaning gases used and the residue material being cleaned (i.e., the cleaning reaction), particular wavelengths can be monitored that are specific to the cleaning reaction. In some embodiments, these particular wavelengths will have intensity peaks within the spectrum response during cleaning and the application 104 can monitor these specific intensity peaks to determine when they are no longer present and the cleaning reaction has completed (i.e., the end point has been reached). In some embodiments, the intensity peaks can be all within a particular range (e.g., all within the infrared (IR) range, ultraviolet (UV) range, visible light range, etc.) or spread over multiple ranges.

When the cleaning endpoint is reached, the application 104 generates a signal to a chamber controller 130 indicating that the chamber is clean and the cleaning process should be stopped (208). In some embodiments, additional cleaning processes can be then be performed to eliminate other residues. In some embodiments, any remaining cleaning reaction byproducts can then be pumped out of the processing chamber 116.

Figure 3A:
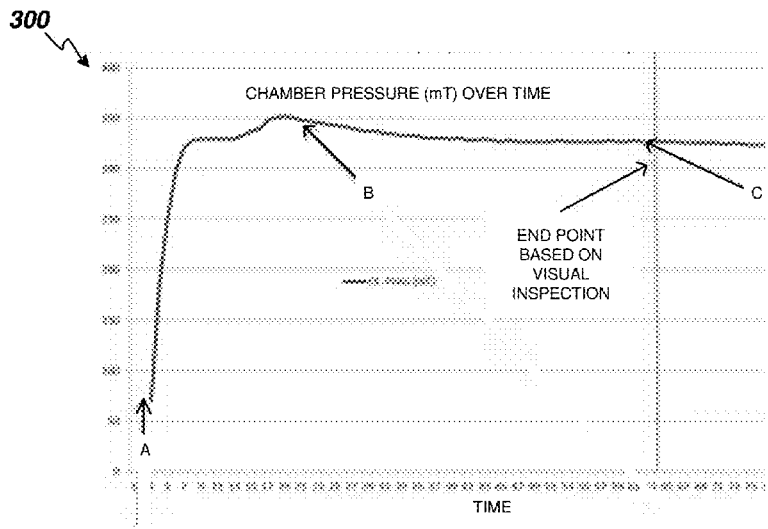
FIG. 3A is a graph of plasma pressure over time within a processing chamber during cleaning according to embodiments of the present invention.
Figure 3B:
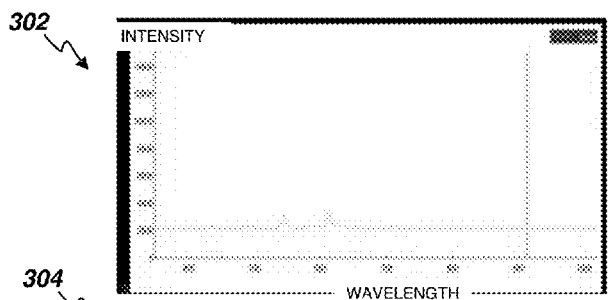
FIGS. 3B to 3D are graphs depicting measured intensity of different wavelengths (i.e., measured spectrum response) at three different points in time during cleaning according to embodiments of the present invention.
Figure 3C:
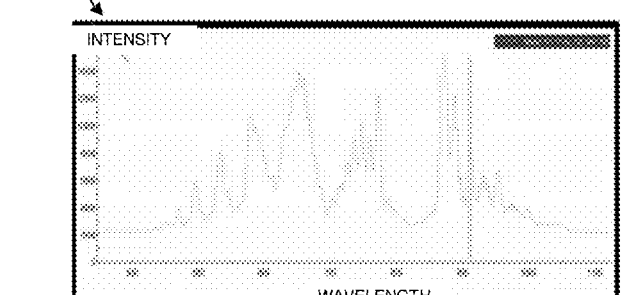
Figure 3D:
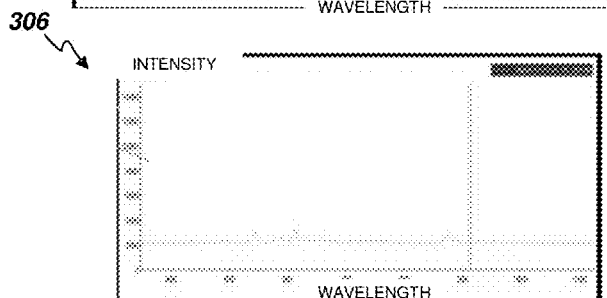

Turning now to FIGS. 3A through 8, example graphs are provided illustrating spectrum responses generated using the methods and apparatus of embodiments of the present invention. FIG. 3A depicts a graph 300 of chamber gas pressure over time before (at point A), during (at point B), and after (at point C) a cleaning cycle. The spectrum response generated using end point detection embodiments of the present invention corresponding to and captured before cleaning begins (i.e., at point A) is depicted in graph 302 of FIG. 3B. The spectrum response generated using end point detection embodiments of the present invention corresponding to and captured during cleaning (i.e., at point B) is depicted in graph 304 of FIG. 3C. The spectrum response generated using end point detection embodiments of the present invention corresponding to and captured after the cleaning reaction has completed (i.e., at point C) is depicted in graph 306 of FIG. 3D. As can be seen, the spectrum response before and after cleaning is relatively flat while the graph 304 representing the spectrum response during cleaning has clear intensity peaks, particularly across the IR range in this example.

Figure 4:
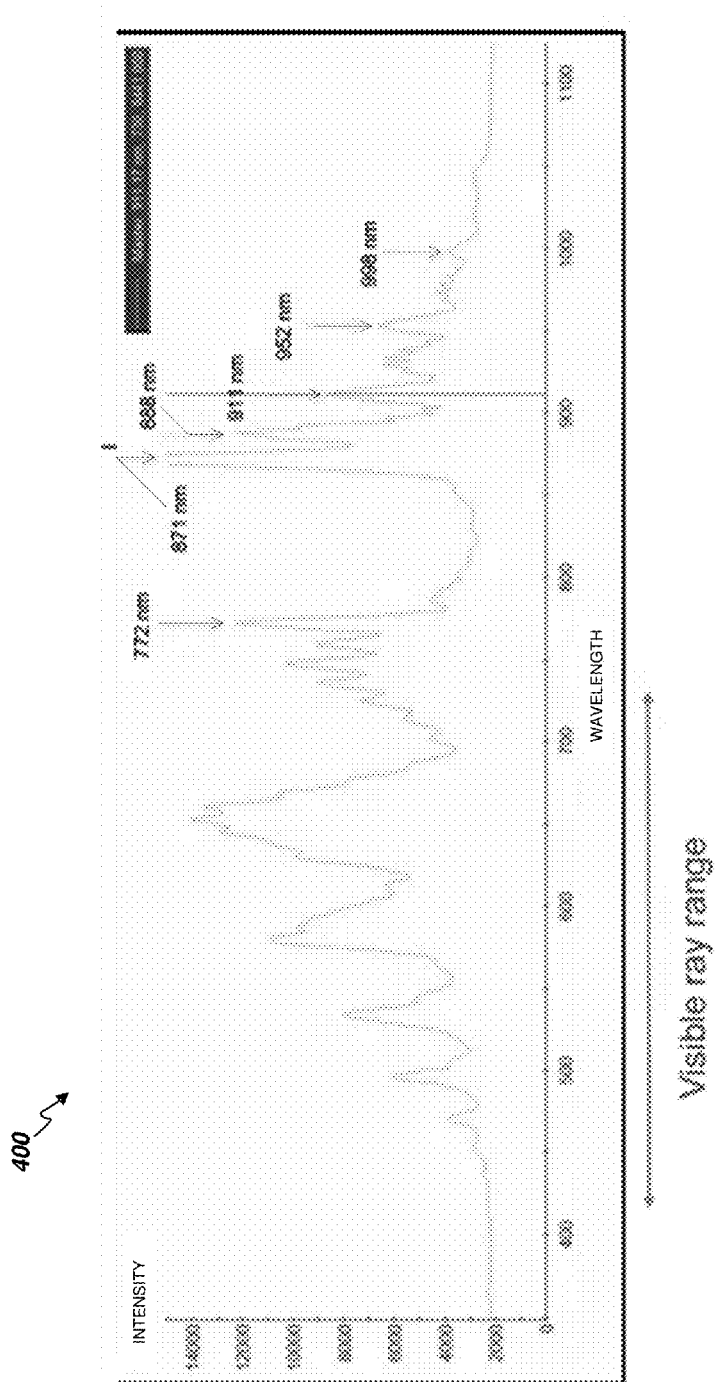
FIG. 4 is a graph depicting measured spectrum response within a processing chamber during cleaning according to embodiments of the present invention.

FIG. 4 depicts a magnified view of an example graph 400 of a spectrum response generated using end point detection embodiments of the present invention corresponding to and captured during cleaning. In this particular example, the major signal peaks (e.g., at 772 nm, 871 nm, 888 nm, 911 nm, 952 nm, and 998 nm) indicating the presence of the cleaning reaction, all occur within a broad IR range (e.g., from approximately 700 nm to approximately 1000 nm.) Note that these particular peaks represent the spectrum response of thin film encapsulation of silicon nitride (TFE-SiN) (i.e., low temperature SiN film) and thin film encapsulation of silicon oxynitride (TFE-SiON) (i.e., low temperature SiON) cleaning reactions. Note that different reactants can have different wavelength intensity peaks.

Figure 5:
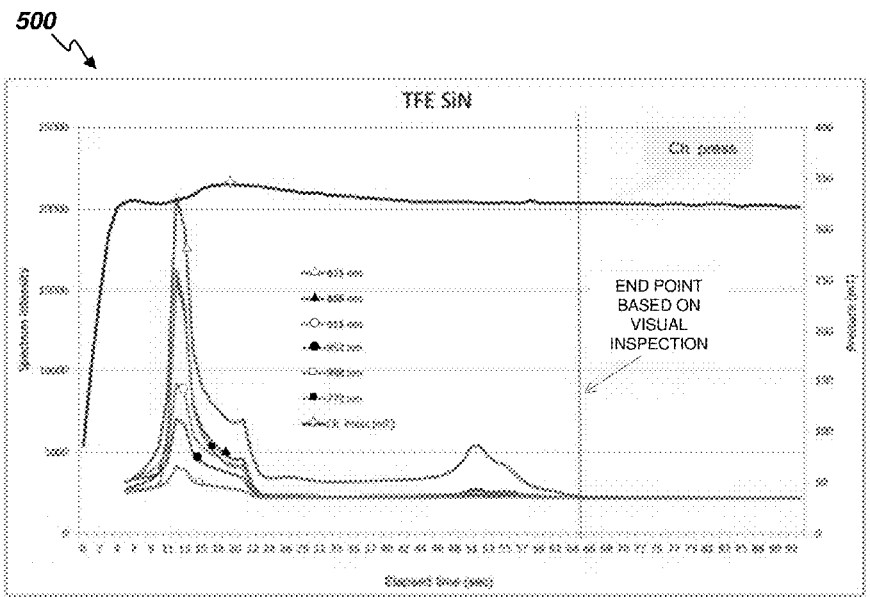
FIG. 5 is a graph depicting a first example plot of chamber pressure over time overlaid with example plots of the intensity of different measured wavelengths over time according to embodiments of the present invention.
Figure 6:
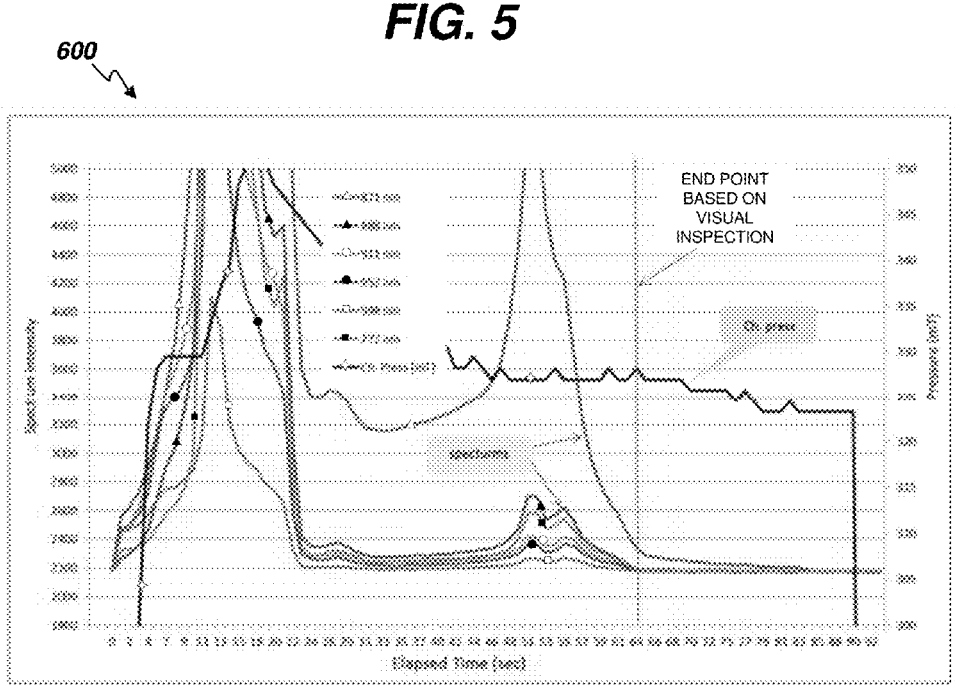
FIG. 6 is a magnified view of the graph of FIG. 5.

FIG. 5 is a graph 500 depicting an example plot of chamber pressure over time during cleaning silicon nitride (SiN) residue with cleaning plasma (e.g., cleaning plasma formed from $C_2F_4$, $NF_3$, $C_3F_6$, etc.) overlaid with example plots of the intensity of six different measured wavelengths over time. The graph 600 in FIG. 6 is a magnified view of the graph 500 in FIG. 5. The wavelengths plotted correspond to the wavelengths with IR range intensity peaks identified in the graph 400 of FIG. 4, namely 772 nm, 871 nm, 888 nm, 911 nm, 952 nm, and 998 nm. Graph 600 of FIG. 6 is a magnified view of graph 500 of FIG. 5. Note that while the chamber pressure was relatively constant, the spectrum intensity is significantly different during cleaning versus after cleaning where the endpoint was determined based on human visual inspection. Note also that different wavelengths can be monitored depending on the reactants (e.g., the film residue to be cleaned and the chemistry of the cleaning plasma). The wavelengths depicted are merely representative examples for the particular residue and cleaning plasma reaction. (i.e., TFE-SiN).

Figure 7:
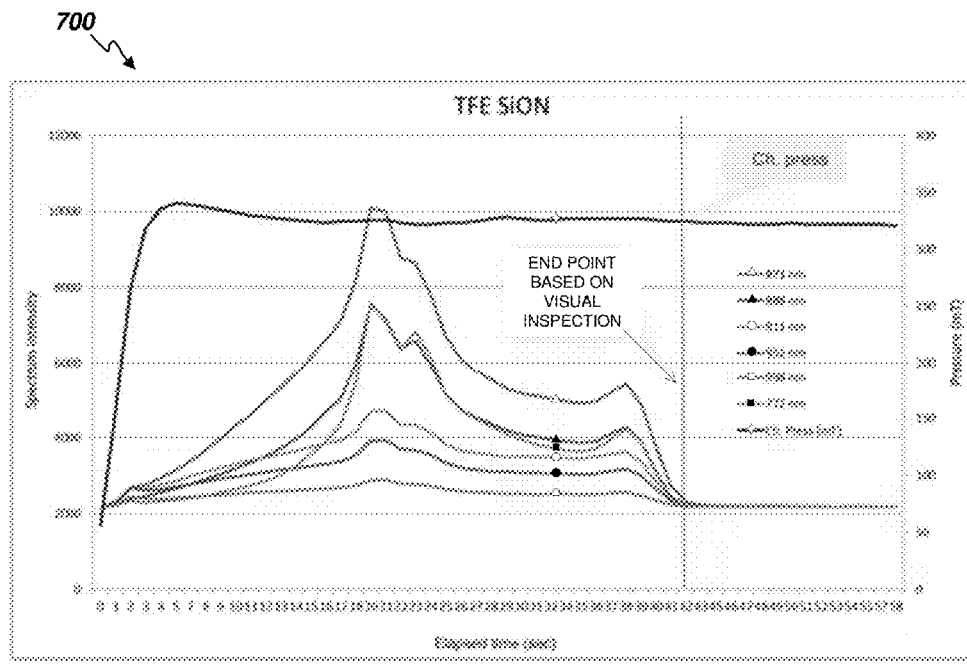
FIG. 7 is a graph depicting a second example plot of chamber pressure over time overlaid with example plots of the intensity of different measured wavelengths over time according to embodiments of the present invention.
Figure 8:
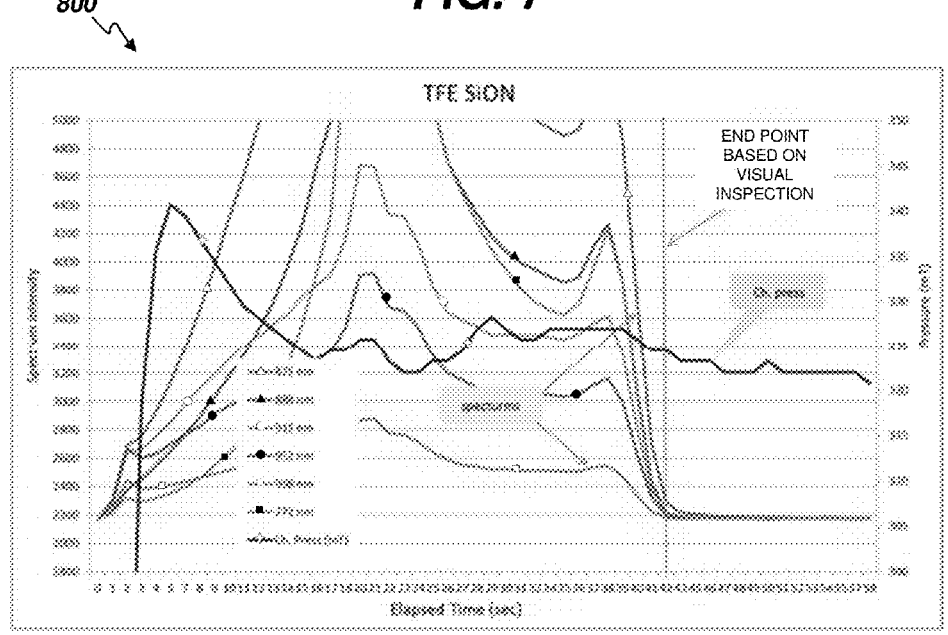
FIG. 8 is a magnified view of the graph of FIG. 7.

FIG. 7 is a graph 700 depicting an example plot of chamber pressure over time during cleaning silicon oxynitride ($SiO_xN_y$) residue with cleaning gas plasma overlaid with example plots of the intensity of six different measured wavelengths over time. The graph 800 in FIG. 8 is a magnified view of the graph 700 in FIG. 7. In some embodiments, anywhere from two to ten wavelengths can be used. The particular example wavelengths plotted correspond to the wavelengths with IR range intensity peaks identified in the graph 400 of FIG. 4, namely 772 nm, 871 nm, 888 nm, 911 nm, 952 nm, and 998 nm. Graph 800 of FIG. 8 is a magnified view of graph 700 of FIG. 7. Note that while the chamber pressure was relatively constant, the spectrum intensity is significantly different during cleaning versus after cleaning where the endpoint was determined based on human visual inspection. Note also that different wavelengths can be monitored depending on the reactants (e.g., the film residue to be cleaned and the chemistry of the cleaning plasma). The wavelengths depicted are merely representative examples for the particular residue and cleaning plasma reaction. (i.e., TFE-SiON).

Numerous embodiments are described in this disclosure, and are presented for illustrative purposes only. The described embodiments are not, and are not intended to be, limiting in any sense. The presently disclosed inventions are widely applicable to numerous embodiments, as is readily apparent from the disclosure. One of ordinary skill in the art will recognize that the disclosed inventions may be practiced with various modifications and alterations, such as structural, logical, software, and electrical modifications. Although particular features of the disclosed inventions may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the invention that must be present in all embodiments. The Title (set forth at the beginning of the first page of this disclosure) is not to be taken as limiting in any way as the scope of the disclosed inventions.

The term "product" means any machine, manufacture and/or composition of matter as contemplated by 35 U.S.C. § 101, unless expressly specified otherwise.

Each process (whether called a method, class behavior, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device, component, structure, or article is described herein, more than one device, component, structure or article (whether or not they cooperate) may alternatively be used in place of the single device, component or article that is described. Accordingly, the functionality that is described as being possessed by a device may alternatively be possessed by more than one device, component or article (whether or not they cooperate).

Similarly, where more than one device, component, structure, or article is described herein (whether or not they cooperate), a single device, component, structure, or article may alternatively be used in place of the more than one device, component, structure, or article that is described. For example, a plurality of computer-based devices may be substituted with a single computer-based device. Accordingly, the various functionality that is described as being possessed by more than one device, component, structure, or article may alternatively be possessed by a single device, component, structure, or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Headings of sections provided in this disclosure are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining, recognizing, and the like.

A "display" as that term is used herein is an area that conveys information to a viewer. The information may be dynamic, in which case, an LCD, LED, CRT, Digital Light Processing (DLP), rear projection, front projection, or the like may be used to form the display.

The present disclosure may refer to a "control system", application, or program. A control system, application, or program, as that term is used herein, may be a computer processor coupled with an operating system, device drivers, and appropriate programs (collectively "software") with instructions to provide the functionality described for the control system. The software is stored in an associated memory device (sometimes referred to as a computer readable medium). While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

A "processor" means any one or more microprocessors, Central Processing Unit (CPU) devices, computing devices, microcontrollers, digital signal processors, or like devices. Exemplary processors are the INTEL PENTIUM or AMD ATHLON processors.

The term "computer-readable medium" refers to any statutory medium that participates in providing data (e.g., instructions) that may be read by a computer, a processor or a like device. Such a medium may take many forms, including but not limited to non-volatile media, volatile media, and specific statutory types of transmission media. Non-volatile media include, for example, optical or magnetic disks and other persistent memory. Volatile media include DRAM, which typically constitutes the main memory. Statutory types of transmission media include coaxial cables, copper wire and fiber optics, including the wires that comprise a system bus coupled to the processor. Common forms of computer-readable media include, for example, a floppy disk, a flexible disk, hard disk, magnetic tape, any other magnetic medium, a CD-ROM, Digital Video Disc (DVD), any other optical medium, punch cards, paper tape, any other physical medium with patterns of holes, a RAM, a PROM, an EPROM, a FLASH-EEPROM, a USB memory stick, a dongle, any other memory chip or cartridge, a carrier wave, or any other medium from which a computer can read. The terms "computer-readable memory" and/or "tangible media" specifically exclude signals, waves, and wave forms or other intangible or non-transitory media that may nevertheless be readable by a computer.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols. For a more exhaustive list of protocols, the term "network" is defined below and includes many exemplary protocols that are also applicable here.

It will be readily apparent that the various methods and algorithms described herein may be implemented by a control system and/or the instructions of the software may be designed to carry out the processes of the present invention.

Where databases and/or data structures are described, it will be understood by one of ordinary skill in the art that (i) alternative database structures to those described may be readily employed, and (ii) other memory structures besides databases may be readily employed. Any illustrations or descriptions of any sample databases/data structure presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models, hierarchical electronic file structures, and/or distributed databases) could be used to store and manipulate the data types described herein. Likewise, object methods or behaviors of a database can be used to implement various processes, such as those described herein. In addition, the databases may, in a known manner, be stored locally or remotely from a device that accesses data in such a database. Furthermore, while unified databases may be contemplated, it is also possible that the databases may be distributed and/or duplicated amongst a variety of devices.

As used herein a "network" generally refers to an information or computing network that can be used to provide an environment wherein one or more computing devices may communicate with one another. Such devices may communicate directly or indirectly, via a wired or wireless medium such as the Internet, LAN, WAN or Ethernet (or IEEE 802.3), Token Ring, or via any appropriate communications means or combination of communications means. Exemplary protocols include but are not limited to: Bluetooth™, Time Division Multiple Access (TDMA), Code Division Multiple Access (CDMA), Global System for Mobile communications (GSM), Enhanced Data rates for GSM Evolution (EDGE), General Packet Radio Service (GPRS), Wideband CDMA (WCDMA), Advanced Mobile Phone System (AMPS), Digital AMPS (D-AMPS), IEEE 802.11 (WI-FI), IEEE 802.3, SAP, the best of breed (BOB), system to system (S2S), or the like. Note that if video signals or large files are being sent over the network, a broadband network may be used to alleviate delays associated with the transfer of such large files, however, such is not strictly required. Each of the devices is adapted to communicate on such a communication means. Any number and type of machines may be in communication via the network. Where the network is the Internet, communications over the Internet may be through a website maintained by a computer on a remote server or over an online data network including commercial online service providers, bulletin board systems, and the like. In yet other embodiments, the devices may communicate with one another over RF, cable TV, satellite links, and the like. Where appropriate encryption or other security measures such as logins and passwords may be provided to protect proprietary or confidential information.

Communication among computers and devices may be encrypted to insure privacy and prevent fraud in any of a variety of ways well known in the art. Appropriate cryptographic protocols for bolstering system security are described in Schneier, APPLIED CRYPTOGRAPHY, PROTOCOLS, ALGORITHMS, AND SOURCE CODE IN C, John Wiley & Sons, Inc. 2d ed., 1996, which is incorporated by reference in its entirety.

It will be readily apparent that the various methods and algorithms described herein may be implemented by, e.g., appropriately programmed general purpose computers and computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software. Accordingly, a description of a process likewise describes at least one apparatus for performing the process, and likewise describes at least one computer-readable medium and/or memory for performing the process. The apparatus that performs the process can include components and devices (e.g., a processor, input and output devices) appropriate to perform the process. A computer-readable medium can store program elements appropriate to perform the method.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

The foregoing description discloses only exemplary embodiments of the invention. Modifications of the above disclosed apparatus and methods which fall within the scope of the invention will be readily apparent to those of ordinary skill in the art. For example, although the examples discussed above are illustrated for cleaning PECVD chambers, embodiments of the invention can be implemented for other chamber types such as etch chambers and chambers for manufacturing flat panel displays, solar panels, and other semiconductor substrates.

Accordingly, while the present invention has been disclosed in connection with exemplary embodiments thereof, it should be understood that other embodiments may fall within the spirit and scope of the invention, as defined by the following claims.

What is claimed is:

1. An apparatus for detecting a cleaning endpoint of a cleaning process performed within a processing chamber, the apparatus comprising:
    a spectrometer adapted to measure a spectrum response over time of a cleaning reaction within a processing chamber during a cleaning process; and
    a zoom lens system coupled to the spectrometer and disposed to focus on a selected area within the processing chamber via a viewport and to amplify intensity of radiation from a cleaning reaction in the selected area during the cleaning process,
    wherein the selected area is chosen based on being an expected location of a last cleaning reaction during the cleaning process within the processing chamber.

2. The apparatus of claim 1 further including a computer operative to execute an application and communicatively coupled to the spectrometer,
    wherein the application includes instructions stored in a memory of the computer and adapted to direct the computer to monitor the spectrum measurements of the spectrometer.

3. The apparatus of claim 2 wherein the instructions include further instructions to generate a signal when the spectrum measurements are below a predefined threshold value indicating a cleaning endpoint has been reached.

4. The apparatus of claim 1 wherein the lens system includes multiple lenses operative to magnify the selected area.

5. The apparatus of claim 1 wherein the selected area is in a corner of the processing chamber.

6. The apparatus of claim 5 wherein the selected area is on at least one of a susceptor, a diffuser plate, and a wall of the processing chamber.

7. The apparatus of claim 1 wherein the cleaning process is a plasma cleaning process.

8. A method of detecting a cleaning endpoint of a cleaning process performed within a processing chamber, the method comprising:
    performing a cleaning process within a processing chamber;
    focusing a zoom lens system on a selected area within the processing chamber via a viewport during the cleaning process;
    amplifying an intensity of radiation from a cleaning reaction in the selected area during the cleaning process; and
    measuring a spectrum response over time of the cleaning reaction within the processing chamber during the cleaning process using a spectrometer coupled to the lens system,
    wherein the selected area is chosen based on being an expected location of a last cleaning reaction during the cleaning process within the processing chamber.

9. The method of claim 8 further including executing instructions stored in a memory of a computer commutatively coupled to the spectrometer and adapted to direct the computer to monitor the spectrum response measured by the spectrometer.

10. The method of claim 9 wherein the instructions include further instructions to generate a signal when the spectrum measurements are below a predefined threshold value indicating a cleaning endpoint has been reached.

11. The method of claim 8 wherein amplifying an intensity of radiation from the cleaning reaction in the selected area includes magnifying the selected area using multiple lenses within the lens system.

12. The method of claim 8 wherein the selected area is in a corner of the processing chamber.

13. The method of claim 8 wherein the selected area is on at least one of a susceptor, a diffuser plate, and a wall of the processing chamber.

14. The method of claim 8 wherein the cleaning process is a plasma cleaning process.

15. A system for processing substrates, the system comprising:
   a processing chamber operative to process substrates; and
   a cleaning endpoint detection apparatus including a spectrometer adapted to measure a spectrum response over time of a cleaning reaction within the processing chamber during a cleaning process and a zoom lens system coupled to the spectrometer and disposed to focus on a selected area within the processing chamber via a viewport and to amplify intensity of radiation from a cleaning reaction in the selected area during the cleaning process,
   wherein the selected area is chosen based on being an expected location of a last cleaning reaction during the cleaning process within the processing chamber.

16. The system of claim 15 further including a computer operative to execute an application and communicatively coupled to the spectrometer,
   wherein the application includes instructions stored in a memory of the computer and adapted to direct the computer to monitor the spectrum measurements of the spectrometer.

17. The system of claim 16 wherein the instructions include further instructions to generate a signal when the spectrum measurements are below a predefined threshold value indicating a cleaning endpoint has been reached.

18. The system of claim 15 wherein the lens system includes multiple lenses operative to magnify the selected area.

19. The system of claim 15 wherein the selected area is in a corner of the processing chamber.

20. The system of claim 15 wherein the selected area is on at least one of a wall, a susceptor, and a diffuser plate of the processing chamber.

* * * * *